United States Patent [19]

Scala, Jr.

[11] 4,275,222

[45] Jun. 23, 1981

[54] BENZOATE ESTER COMPOSITIONS

[75] Inventor: Thomas L. Scala, Jr., West Milford, N.J.

[73] Assignee: Finetex, Inc., Elmwood, N.J.

[21] Appl. No.: 74,071

[22] Filed: Sep. 14, 1979

Related U.S. Application Data

[63] Continuation-in-part of Ser. No. 949,630, Oct. 10, 1978, abandoned.

[51] Int. Cl.$^3$ .............................................. C07C 69/78
[52] U.S. Cl. ...................................... 560/103; 424/60; 424/63; 424/64; 424/68; 424/70; 424/172; 252/DIG. 5
[58] Field of Search ........................................ 560/103

[56] References Cited

U.S. PATENT DOCUMENTS

| | | | |
|---|---|---|---|
| 2,428,450 | 10/1947 | Eitelman | 560/103 |
| 3,506,704 | 4/1970 | Miller et al. | 560/103 |
| 4,088,598 | 5/1978 | Williams | 252/135 |

OTHER PUBLICATIONS

Kirk–Othmer, Encyclopedia of Chemical Technology, 3rd Ed. vol. 1, pp. 716–739, 747–749, 751.
Drug & Cosmet. Ind., 1970, 107(2), p. 36, (Aug. 1970).

*Primary Examiner*—Jane S. Myers
*Attorney, Agent, or Firm*—Weingram & Klauber

[57] ABSTRACT

A composition of matter, comprising the benzoic acid esters of a mixture of $C_{12}$, $C_{13}$, $C_{14}$ and $C_{15}$ linear primary alcohols. The alcohol mixture may comprise by weight from about 13 to 31% of said $C_{12}$ alcohol, 28 to 44% of said $C_{13}$ alcohol, 17 to 40% of said $C_{14}$ alcohol, and 12 to 19% of said $C_{15}$ alcohol. The alcohol mixture preferably comprises by weight from about 23 to 31% of said $C_{12}$ alcohol, 32 to 44% of said $C_{13}$ alcohol, 17 to 23% of said $C_{14}$ alcohol, and 12 to 18% of said $C_{15}$ alcohol. Compositions in accordance with the invention are useful as diluents, solvents, plasticizers, liquid carriers, and the like.

1 Claim, No Drawings

BENZOATE ESTER COMPOSITIONS

This application is a continuation-in-part of my co-pending application, Ser. No. 949,630, filed Oct. 10, 1978, now abandoned and entitled "Improved Ester Compositions", which application is assigned to the assignee of the instant application.

BACKGROUND OF THE INVENTION

This invention relates generally to novel chemical compositions, and more specifically relates to novel ester compositions useful as diluents, solvents, plasticizers, liquid carriers, and the like.

SUMMARY OF THE INVENTION

The organic liquid compositions of the invention comprise the benzoic acid esters of a mixture of $C_{12}$, $C_{13}$, $C_{14}$ and $C_{15}$ linear primary alcohols. These benzoates are the reaction products of benzoic acid with a mixture of the aforementioned linear primary alcohols. The alcohol mixture may generally comprise by weight from about 13 to 31% of said $C_{12}$ alcohol, 28 to 44% of said $C_{13}$ alcohol, 17 to 40% of said $C_{14}$ alcohol, and 12 to 19% of said $C_{15}$ alcohols. Preferably the alcohol mixture comprises by weight from about 23 to 31% of said $C_{12}$ alcohol, 32 to 44% of said $C_{13}$ alcohol, 17 to 23% of said $C_{14}$ alcohol, and 12 to 18% of said $C_{15}$ alcohol.

The alcohol precursors used in preparing the products of the invention include primary alcohols having a proportion of branching at the 2-carbon position. One class of such alcohols are primary alcohols of formula ROH, where R is a primary alkyl group with from 12 to 15 carbon atoms, which is additionally represented by the formula:

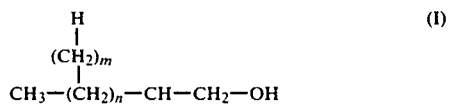

$$\text{CH}_3-(\text{CH}_2)_n-\overset{\overset{\displaystyle H}{|}\overset{(CH_2)_m}{|}}{\text{CH}}-\text{CH}_2-\text{OH} \quad (I)$$

where m is a whole number from 0 to 6 inclusive, and n is a whole number from 6 to 12 inclusive such that $m+n+3=12,13,14$ or 15. In such alcohols at least 70% by weight of the alcohol of each specific chain length is linear (i.e. $m=0$) and the branching (if any) comprises about 50% of methyl groups with smaller amounts of ethyl, propyl, butyl, amyl and hexyl groups. These alcohols shall hereinafter be referred to in this specification by the term "linear primary alcohol", and are conveniently produced by the reaction of carbon monoxide and hydrogen with linear olefins having from 11 to 14 carbon atoms. The direct hydroformylation of olefins to give alcohols has been described, for example, in Kirk-Othmer, *Encyclopedia of Chemical Technology*, 3rd Ed., Vol. 1, p. 751, and references incorporated therein.

Blends of linear primary alcohols of the above type are manufactured by and commercially available from Shell Chemical Company, Houston, Tex., under the name NEODOL ®. These alcohols are also manufactured in the U.K. and Japan, using the same technology, and are marketed outside North America by Shell International Company, London, under the name DOBANOL.

The benzoate ester compositions of the present invention are among other things, characterized by a surprisingly low odor. This is a most significant property for numerous application of the present compositions, e.g. as solvents or carriers for fragrances or the like, or as solvents or carriers for components of toiletry or cosmetic products, for dyestuffs, etc., in which instances, the said compositions may comprise or ultimately be incorporated in various toiletry products, textiles or so forth—i.e. in products where absence of odor is of paramount importance for consumer acceptance.

The compositions further, display an unusual lack of greasiness, an extremely low toxicity, a low cloud point, and excellent ability to form gels of relatively high viscosity with commonly used suspending agents such as a quaternized hectorate. All such properties are of great importance for typical applications to which ester products of the present type are placed.

DESCRIPTION OF PREFERRED EMBODIMENT

The following Examples I through III, set forth typical procedures and results yielded in the course of preparing the benzoate compositions of the present invention:

EXAMPLE I

A mixture of 227.7 parts (1.1 mol) of NEODOL 25, 122.0 parts (1.0 mol) of benzoic acid and 1.7 parts of methane sulfonic acid (as a catalyst) was stirred and heated under nitrogen to a temperature of 170° C. while collecting any distillate formed. NEODOL 25 is one of the above-discussed products of Shell Chemical Co., and is a mixture of $C_{12}$, $C_{13}$, $C_{14}$, and $C_{15}$ linear primary alcohols in weight percentages within the preferred ranges above set forth, i.e. 23 to 31% of the $C_{12}$ said alcohol, 32 to 44% of the $C_{13}$ said alcohol, 17 to 23% of the $C_{14}$ said alcohol, and 12 to 18% of the $C_{15}$ said alcohol. Thus, in a typical analysis of a NEODOL 25 sample, it was found to include by weight 29.4% of $C_{12}$, 36.7% of $C_{13}$, 18.3% of $C_{14}$ and 15.5% of the $C_{15}$ linear primary alcohol.

When no more distillate came over and the acidity was less than 3 mg, it was cooled to 50° C. and washed with water and soda ash solution to a pH of 8–9. After washing again with a dilute salt solution, the ester layer was separated and heated under vacuum to remove traces of water. The benzoate product was a clear liquid with a surprisingly low odor.

EXAMPLE II

A mixture of 207 parts (1.0 mol) of NEODOL 25, 122 parts (1.0 mol) of benzoic acid and 1.6 parts of methane sulfonic acid catalyst was heated under nitrogen to 170°–175° C. with stirring. The reaction was held at this temperature for approximately 4 hours, collecting distillate formed until acidity dropped below 5 mg. The product was then cooled to 50° C., neutralized, washed and vacuum stripped to remove any excess residual water. The final benzoate product was an almost colorless liquid with very low odor.

EXAMPLE III

Example IV was repeated using 207 g (1.0 mol) of NEODOL 25, 128.1 g (1.5 mol) of benzoic acid and 1.6 g of methane sulfonic acid. The reaction was run until acidity dropped below 10 mg. It was then cooled, neutralized, washed and vacuum stripped as in Example II, resulting in an almost colorless liquid benzoate product with very low odor.

For typical applications to which the ester products of this invention are placed, there are five characteristics which are of utmost importance. These are: (1) lack of greasiness; (2) extremely low toxicity; (3) low cloud point; (4) virtual absence of odor; and (5) ability to form gels of relatively high viscosity with suspending agents such as a quaternized hectorite or stearalkonium hectorite. In the following Examples, these characteristics are exemplified for the products of the invention, and are compared to corresponding characteristics in prior art compositions.

Referring therefore to item (1) above, "greasiness" is a term applied to a product or a formula containing such a product, that is suggestive of or resembles something greased, i.e. it has a slick unctuous character, which manifests its presence easily, even to the layman. Applied to skin, for example, it produces a distinct gloss, which although not considered too detrimental in itself, also results in a slick greased hand, resulting in a messy, unsightly condition which offends consumers. Examples of products producing these effects are mineral oil, isopropyl myristate (IPA), and lanolin.

Although the presence of these last materials is at times necessary in the development of a toiletry product, manufacturers spend enormous effort in an attempt to diminish this one characteristic which is abhorent to good product development, that is greasiness. What is essentially sought after is an emollient having all the characteristics of an oil, but lacking that one particular characteristic of all oils, i.e. greasiness and the gloss associated with the presence of grease.

EXAMPLE IV

A comparison of the products of the present invention was undertaken with a single benzoate ester falling within the carbon chain length range encompassed in the mixtures of the invention. In particular, there was utilized in this comparison, samples of the products of the invention corresponding to those produced in Example I of the present specification. As is indicated in that Example, the said product comprises the benzoic acid esters of a mixture of $C_{12}$, $C_{13}$, $C_{14}$, and $C_{15}$ linear primary alcohols of specified percentages. This product was compared with a myristyl ($C_{14}$) benzoate, which was prepared by a similar procedure to that described in Example I, i.e. by reaction of myristyl alcohol with benzoic acid under conditions essentially corresponding to those of Example I.

It was found that the myristyl benzoate is a much heavier product, virtually a solid at ambient room temperature, i.e. 65°–70° F. The application of a drop of myristyl benzoate to the skin was found to be still evident one-half hour after rub-in of same, whereas the product of the invention, although giving the feeling of emolliency, did not display the sheen associated with the presence of a greasy substance as did the myristyl benzoate.

It may be noted that the foregoing result is deemed completely unexpected, since the product of the invention may be thought to include as one component thereof a $C_{14}$ myristyl benzoate; and yet in the mixture defined in the invention the properties are completely dissimilar in the extremely important characteristic just discussed.

EXAMPLE V

In this Example, further evaluation of oiliness and glossiness was effected for compositions in accordance with the invention, in comparison with products comprising mixes of $C_{14}$ and $C_{15}$ benzoates and of $C_{12}$ and $C_{13}$ benzoates. More specifically, four products were compared: (1) A composition as in Example I; (2) A composition prepared by the reaction of Neodol 23 (a mixture of approximately 32% of the $C_{12}$ and 68% of the $C_{13}$ linear primary alcohols) with benzoic acid, essentially under the conditions of Example I; (3) A composition prepared by the reaction of Neodol 45 (a mixture of approximately 68% of $C_{14}$ and 32% of $C_{15}$ linear primary alcohols by weight) with benzoic acid, essentially under the conditions of Example I; and (4) A composition prepared by mixing on a 1:1 weight basis Neodol 23 and Neodol 45 (which yields a mix by weight of approximately 16% of the $C_{12}$ linear primary alcohol, 34% of the $C_{13}$ alcohol, 34% of the $C_{14}$ alcohol, and 16% of the $C_{15}$ alcohol), and reacting that mix with benzoic acid essentially under the conditions of Example I.

The tests conducted were subjective in nature—10 individuals were requested to evaluate the above-mentioned characteristics using a scale of 1 to equal "least" to 4 for "most". The results are set forth in Table I below, from which it will be seen that the compositions of the invention are far superior to products including other mixes of $C_{12}$–$C_{15}$ benzoates. It will also be seen that the compositions falling within the preferred ranges of the invention, i.e. the composition of Example I, is much superior to the composition derived from the 23/45 mix.

TABLE I

| Product | Oiliness | Gloss |
| --- | --- | --- |
| Composition of Example I | 1 | 1 |
| Neodol 23 benzoates | 3 | 3 |
| Neodol 45 benzoates | 3 | 4 |
| Neodol 23/45 (1:1) benzoates | Above 2 | Above 1 |

EXAMPLE VI

The second of the above-mentioned criteria, "cloud point", refers to the temperature at which a waxy solid material appears as the liquid composition being examined is cooled. Cloud points are also associated with pour points, which is the lowest temperature at which a liquid will flow when a container is inverted. In all cases as the temperature is lowered, the cloud point is detected first, with the pour point being generally 5°–25° F. lower.

It is an important characteristic of formulation development for toiletries and the like to utilize a product that has as low a cloud point as possible. This is a necessary requirement to prevent irreversible changes from occuring during the lifetime of a toiletry product exposed to varying ambient temperatures of e.g. $-15°$ C. to 48° C.

Whereas myristyl benzoate has a cloud point determined at 21° C., the product of Example I of the present invention, was found to have an astonishingly low cloud point of below 0° C., and a pour point approaching $-14°$ C. This is of enormous importance for storage of large quantities of a particular raw material in unheated warehouses during winter.

EXAMPLE VII

Referring now to the characteristic of odor: Lack of odor is of enormous importance in the development of consumer-oriented products. Many emollients have a characteristic odor that is obnoxious and in many cases difficult to mask. Where masking is possible, it is accomplished only at great expense.

Completely unexpectedly, it has been found that the products of the present invention are for all practical purposes lacking in odor. A direct comparison was made e.g. between the product of Example I and myristyl benzoate—and yielded startling results. Myristyl benzoate thus has a pungent fatty odor, making it unacceptable, e.g. as a fragrance diluent, whereas the product of the invention is completely bland.

The significance of this lack of odor may be appreciated (e.g. in fragrance applications) by observing that all formulas have a minimum fragrance level (MFL), at which the formula no longer has an inherent odor. However, even at this MFL the notes of the fragrance itself are not noticeable. A slight increase in fragrance level must be effected to be able to detect the fragrance oil added. Based on a (typical) $8.00 per pound fragrance oil, and using the Example I product of the invention, a level of 0.25% can be used to overcome the inherent odor of the formula, to establish a detectable level of fragrance. Myristyl benzoate on the contrary, requires a figure much in excess of 0.25%—and here it must be borne in mind that for every 0.1 pound increase, the cost per hundred pounds of finished product (in this hypothetical example) increases eighty cents.

EXAMPLE VIII

In this Example, further evaluation of odor was effected for compositions in accordance with the invention, in comparison with products comprising mixes of $C_{14}$ and $C_{15}$ benzoates and of $C_{12}$ and $C_{13}$ benzoates. More specifically, the four products set forth in Example V were compared by again requesting ten individuals to evaluate odor using a scale of 1 to equal "least" to 4 "most". The results are set forth in Table II below, from which it will be again seen that the compositions of the invention are far superior to products including other mixes of $C_{12}$-$C_{15}$ benzoates. It will also again be seen that the compositions falling within the preferred ranges of the invention, i.e. the composition of Example I, is superior to the composition derived form the Neodol 23/45 mix.

TABLE II

| Product | Odor |
| --- | --- |
| Composition of Example 1 | 1 |
| Neodol 23 benzoates | Above 2 |
| Neodol 45 benzoates | 3 |
| Neodol 23/45 (1:1) benzoates | Above 1 |

EXAMPLE VIII

The fourth characteristic above-listed, is gel formulation. This refers to the ability of an emollient oil to form gels with suspending agents such as quaternized hectorite (such as Bentone 38) or stearalkonium (Bentone 37). This is a desirable characteristic as it provides the formulator a means of suspending many actives such as aluminum chlorhydrol and pigments in anhydrous systems. The former is particularly useful in aerosol and stick type antiperspirants; the latter in such products as lipsticks, stick rouge, and other facial makeup products.

Such gels should exhibit absence of syneresis, i.e. the contraction of a gel on standing with the subsequent exudation of liquid; high viscosity; temperature stability; and ability to suspend matter. The presence of syneresis negates the bulk storage of a Bentone Gel (10% stearalkonium hectorite or quaternium-18 hectorite suspension in an anhydrous solvent), as it requires equipment and expertise not normally available in many manufacturing facilities to enable the gel to be reconstituted to a homogeneous condition prior to use.

The viscosity of a gel is dependent on the polarity of the organic liquid it is suspended in. The more polar the liquid, the lower the viscosity. Non-polar or low polarity organic liquids result in higher viscosities. Completely non-polar liquids may present a problem in that too high viscosities result with a low percentage of a gellant. Upon further dilution (as normally occurs in formulation work), the ability to suspend matter can be lost in there instance.

In tests, it was found that when a semi-solid such as the aforementioned myristyl benzoate, is used as the organic liquid, a requirement is created for an abnormal amount of mechanical, chemical, and thermal energy; and this results in a gel with abnormally high viscosities.

Desirably, basic gel concentrates and formulations containing same, should show stability to a wide range of temperatures without phase separation—which would destroy the gel viscosity and suspending capabilities. In addition, the basic function of such gels is to suspend an active material present in a formulation as a particulate matter. In a system such as aerosol antiperspirants, the active is aluminum chlorhydrol, present as insoluble particulates, with a particle size ranging from submicron to about 50 microns. Before use, the container is shaken to re-disperse the particulates in suspension as to provide the proper dosage of activities. Redispersion should be immediate, complete, and last for a period of time sufficient for proper application. Longer times are indeed more beneficial as it provides a lower misuse factor.

EXAMPLE IX

With most solvents, including specifically the aforementioned myristyl benzoate, it was found that settling occurs within 60 to 90 seconds. Completely unexpectedly, it was, however, found that when the products of the present invention (specifically including the product of Example I) were so used, settling times increased to 4 to 7 minutes. Further, the products when settled, did not hard-pack—so that they were easily re-dispersed. This property of the esters of the present invention is completely unexpected; and is of enormous utility for typical applications of the said esters.

EXAMPLE X

Turning to the enumerated item (5), i.e. toxicity: Products of the type in which the present esters are incorporated, invariably come in contact with the consumer. Great care and caution are therefore exercised by manufacturers, and by state and federal agencies to insure the use of raw materials that are innocuous and free from harmful contaminants. Toxicity studies pertinent to the present compositions were accordingly conducted. It was unexpectedly found that (for the product of Example I) the results on acute oral toxicity (rate), $LD_{50}$, was 34.5 g/kg of body weight. Industry normally considers a product having an $LD_{50}$ of greater than 5 g/kg as adequate. These results establish extremely low toxicity. While precisely comparative data for myristyl benzoate is not available, the significance of the present finding may be appreciated by noting that the very commonly used ester, butyl benzoate has an $LD_{50}$ of 3.5 g/kg of body weight. Thus the product of the invention has a toxicity only 1/10th that of a chemically somewhat analogous product—which is extremely unexpected.

EXAMPLE XI

In this Example, the emulsifying properties of the compositions of the invention were compared to various commonly used solvents and to mixes of benzoates not within the invention.

Tests were conducted by adding exactly 20 ml of toluene to 20 ml of the test solvent in a glass stoppered cylinder and shaking to mix. When mixed, 20 ml of water was then added, the resulting mixture warmed to 40° C. and shaken 30 times. This was allowed to stand for 15 minutes and the upper layer analyzed for water content by the Karl Fisher titration method. Results are set forth in the following Table III:

TABLE III

| Test Solvent | % Water in Oil Phase (upper layer; by K-F Method) |
| --- | --- |
| Composition of Example I | 0.69 |
| IPM (isopropyl myristate) | 0.12 |
| IPP (isopropyl polmitate) | 0.66 |
| Mineral Oil | less than 0.10 |
| Octyl Isononanoate | 0.26 |
| Neodol 23 benzoates* | 0.28 |
| Neodol 25* | 0.28 |
| Mix (50:50) of Neodol 23 and Neodol 25* | 0.36 |

*as in Examples V and VIII

These results show that the Example I composition has greater emulsifying properties than the other commonly used solvents, and considerably better such properties than the Neodol 23 or Noedol 25 compositions. Of further interest, is that the blend of Neodol 23 and Neodol 25, provides considerably less emulsification than the Example I composition—the latter being, of course, within the preferred compositional range of the invention.

EXAMPLE XII

The antifoaming properties of the compositions of the invention were compared to other standard products, and to other formulations of benzoate esters not within the invention. Although the terms "defoamer" and "antifoam" are often used interchangeably, a defoamer destroys the foam from above once it exists, whereas an antifoamer prevents the foam from forming initially. To function effectively a defoamer or antifoam must be aloof of the system, that is "half-in, half-out". If it is too far "in" (i.e. dispersible or soluble) it will not destroy foam. If it is too far "out" (i.e. not dispersible or insoluble in the system) it is equally objectionable.

In the procedure utilized, 50 mg of RUETERG 97S (a mono ethanol amine-dodecyl benzene sulfonic acid product of Finetex, Inc.) was added to 300 ml of water contained in a 1000 ml graduated cylinder along with 50 mg of a test product. Air was bubbled through the system for 10 minutes, after which the foam height was taken. The results are as follows (Table IV):

TABLE IV

| Test Product | Foam Height |
| --- | --- |
| Composition of Example I | 50 ml |
| IPM | 500 ml |
| Silicone Oil | overflow |
| Antifoam B* | 10 ml |
| Neodol 23 | 80 ml |
| Neodol 25 | 50 ml |

*proprietary antifoam product of Dow-Corning.

The products of the invention, although not quite as good as the commercial products, are seen to be unexpectedly superior to a common ester such as IPM.

EXAMPLE XIII

To further demonstrate the uniqueness of the compositions of the invention, a series of simple formulas were prepared comparing the appearance, pH and viscosities of various toiletry and cosmetic products formulated with the compositions of the invention, and with other esters and the like which commonly function in similar capacities in the products considered. The products specifically considered included a hair cream, hand cleaner, dispersible bath oil, suntan oil, floating bath oil, and a brilliantine. These are deemed to be highly representative of formulations wherein the products of the invention find widespread application. The results are set forth in Tables V and VI below:

TABLE V

| | HAIR CREAM | | HAND CLEANER | |
| --- | --- | --- | --- | --- |
| Component | A Parts | B Parts | C Parts | D Parts |
| Pluronic F-127* | 5.0 | 5.0 | — | — |
| Pluronic L-92* | 2.5 | 2.5 | — | — |
| Veegum** | 1.0 | 2.0 | — | — |
| Cetyl Alcohol | — | — | 2.0 | 2.0 |
| Composition of Ex. I | — | 25.0 | — | 25.0 |
| Neodol 23 benzoates | 25.0 | — | 25.0 | — |
| Solulan 75+ | — | — | 3.0 | 3.0 |
| Solulan 98+ | 5.0 | 5.0 | — | — |
| Glyceryl monostearate | 2.0 | 2.0 | 5.0 | 5.0 |
| Stearic Acid | — | — | 5.0 | 5.0 |
| Myristyl Alcohol | — | — | — | — |
| Vancide 89 RE++ | 0.5 | 0.5 | — | — |
| Citric Acid | 0.1 | 0.1 | — | — |
| Glycerin | — | — | 5.0 | 5.0 |
| Triethanolamine | — | — | 2.0 | 2.0 |
| Water | 58.7 | 58.7 | 53.0 | 53.0 |
| Appearance | White Liquid | White Liquid | Stiff off-white paste | as A, but creamier |
| pH | 5.0 | 5.5 | 8.2 | 8.7 |
| Viscosity, cps | 130 | 912 | 27,600 | 37,200 |

*Block polymer surfactant (BASF Wyandotte)
**magnesium aluminum silicate (RT Vanderbilt)
+a lanolin-based auxiliary emulsifier (Amerchol Corp.)
++mercaptain fungicide (RT Vanderbilt)
Evaluation:
Formula A is too thin, difficult to apply.
Formula B is suitable.
Formula C is granular in appearance
Formula D is an appealing stiff cream

TABLE VI

| | Dispersible Bath Oil | | Sun Tan Oil | | Floating Bath Oil | | Brilliantine | |
| --- | --- | --- | --- | --- | --- | --- | --- | --- |
| | E Parts | F Parts | G Parts | H Parts | I Parts | J Parts | K Parts | L Parts |
| Modulan* | 5.0 | 5.0 | — | — | — | — | — | — |
| Acetulan** | 5.0 | 5.0 | — | — | — | — | 5.0 | 5.0 |
| Neodol 23 benzoates | 60.0 | — | 85.8 | — | 95.0 | — | 95.0 | — |
| Compos. of Ex. I | — | 60.0 | — | 85.8 | — | 95.0 | — | 95.0 |

TABLE VI-continued

|  | Dispersible Bath Oil | | Sun Tan Oil | | Floating Bath Oil | | Brilliantine | |
| --- | --- | --- | --- | --- | --- | --- | --- | --- |
|  | E Parts | F Parts | G Parts | H Parts | I Parts | J Parts | K Parts | L Parts |
| Ethyl Alcohol | — | — | 10.0 | 10.0 | — | — | — | — |
| Escalol 507 + | — | — | 1.2 | 1.2 | — | — | — | — |
| Mineral Oil | 24.5 | 24.5 | — | — | — | — | — | — |
| Lanoil*** | — | — | 2.5 | 2.5 | — | — | — | — |
| PEG 400 Dilaurate + + | 5.0 | 5.0 | — | — | — | — | — | — |
| Pluronic L-92 | — | — | — | — | 1.0 | 1.0 | — | — |
| Appearance | Hazy Yellow | Clear Yellow | Hazy Tan | Clear Straw | Cloudy | Clear | Hazy | Clear |
| pH | 5.5 | 6.0 | 5.7 | 6.2 | 5.7 | 6.3 | 5.6 | 6.2 |
| Viscosity cps | 42 | 45 | — | — | — | — | — | — |

*Modified lanolin (Amerchol Corp.)
**Lanolin based derivative (Amerchol Corp.) ˙ Amino isooctyl PBA (Van Dyk & Co.)
***Lanolin oil (Lanotex)
˙ ˙ Polyethylene glycol (Diamond Shamrock Corp.)
Evaluation:
Formulas E, G, I, and K are not suitable due to their hazy appearance and odor.
Formulas F, H, J and L are suitable, due to their crystal clarity and lack of odor.

While the present invention has been particularly set forth in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

I claim:

1. A composition of matter consisting of the benzoic acid esters of a mixture by weight of from about 23 to 31% of $C_{12}$, 32 to 44% of $C_{13}$, 17 to 23% of $C_{14}$, and 12 to 18% of $C_{15}$ linear primary alcohols.